(12) United States Patent
Chomas et al.

(10) Patent No.: US 8,500,775 B2
(45) Date of Patent: *Aug. 6, 2013

(54) PROTECTION DEVICE AND METHOD AGAINST EMBOLIZATION AGENT REFLUX

(75) Inventors: James E. Chomas, Denver, CO (US); Leonard Pinchuk, Miami, FL (US); John Martin, Miami, FL (US); Aravind Arepally, Atlanta, GA (US)

(73) Assignee: Surefire Medical, Inc., Westminster, CO (US)

( * ) Notice: Subject to any disclaimer, the term of this patent is extended or adjusted under 35 U.S.C. 154(b) by 387 days.

This patent is subject to a terminal disclaimer.

(21) Appl. No.: 12/829,565

(22) Filed: Jul. 2, 2010

(65) Prior Publication Data
US 2011/0130657 A1    Jun. 2, 2011

Related U.S. Application Data

(60) Provisional application No. 61/266,068, filed on Dec. 2, 2009.

(51) Int. Cl.
*A61M 29/00* (2006.01)

(52) U.S. Cl.
USPC ........................................ 606/200; 604/96.01

(58) Field of Classification Search
USPC .............. 623/1.24–1.26, 2.11, 2.18; 606/200; 604/96.01, 247
See application file for complete search history.

(56) References Cited

U.S. PATENT DOCUMENTS

| | | |
|---|---|---|
| 4,738,740 A | 4/1988 | Pinchuk et al. |
| 5,234,425 A | 8/1993 | Fogarty et al. |
| 5,893,869 A | 4/1999 | Barnhart et al. |
| 5,895,399 A | 4/1999 | Barbut et al. |
| 5,910,154 A | 6/1999 | Tsugita et al. |
| 5,911,734 A | 6/1999 | Tsugita et al. |
| 6,010,522 A | 1/2000 | Barbut et al. |
| 6,027,520 A | 2/2000 | Tsugita et al. |
| 6,042,598 A | 3/2000 | Tsugita et al. |
| 6,059,745 A | 5/2000 | Gelbfish |
| 6,165,200 A | 12/2000 | Tsugita et al. |
| 6,168,579 B1 | 1/2001 | Tsugita |
| 6,179,851 B1 | 1/2001 | Barbut et al. |
| 6,235,044 B1 | 5/2001 | Root et al. |
| 6,258,120 B1 | 7/2001 | McKenzie et al. |
| 6,306,074 B1 | 10/2001 | Waksman et al. |
| 6,306,163 B1 | 10/2001 | Fitz |
| 6,309,399 B1 | 10/2001 | Barbut et al. |
| 6,361,545 B1 | 3/2002 | Macoviak et al. |
| 6,371,969 B1 | 4/2002 | Tsugita et al. |

(Continued)

OTHER PUBLICATIONS

A Study of the Geometrical and Mechanical Properties of a Self-Expandig Metallic Stent—Theory and Experiment, Dr. Michael R. Jedwab, Claude O. Clerc, Journal of Applied Biomaterials, vol. 4, Issue 1, pp. 77-85, Spring 1993.

(Continued)

*Primary Examiner* — Gary Jackson
*Assistant Examiner* — Lindsey Bachman
(74) *Attorney, Agent, or Firm* — Gordon & Jacobson, PC

(57) ABSTRACT

An apparatus is provided that is useful in an embolization procedure and enables substantially unrestricted forward flow of blood in a vessel and reduces or stops reflux (regurgitation or backward flow) of embolization agents which are introduced into the blood. A method of using the apparatus is also provided.

27 Claims, 7 Drawing Sheets

U.S. PATENT DOCUMENTS

| | | | |
|---|---|---|---|
| 6,371,971 B1 | 4/2002 | Tsugita et al. | |
| 6,383,206 B1 | 5/2002 | Gillick et al. | |
| 6,395,014 B1 | 5/2002 | Macoviak et al. | |
| 6,436,112 B2 | 8/2002 | Wensel et al. | |
| 6,443,926 B1 | 9/2002 | Kletschka | |
| 6,485,456 B1 | 11/2002 | Kletschka | |
| 6,485,502 B2 | 11/2002 | Don Michael et al. | |
| 6,499,487 B1 | 12/2002 | McKenzie et al. | |
| 6,530,935 B2 | 3/2003 | Wensel et al. | |
| 6,533,800 B1 | 3/2003 | Barbut | |
| 6,537,294 B1 | 3/2003 | Boyle et al. | |
| 6,537,297 B2 | 3/2003 | Tsugita et al. | |
| 6,540,722 B1 | 4/2003 | Boyle et al. | |
| 6,551,303 B1 | 4/2003 | Van Tassel et al. | |
| 6,582,396 B1 | 6/2003 | Parodi | |
| 6,589,264 B1 | 7/2003 | Barbut et al. | |
| 6,592,546 B1 | 7/2003 | Barbut et al. | |
| 6,607,506 B2 | 8/2003 | Kletschka | |
| 6,620,148 B1 | 9/2003 | Tsugita | |
| 6,635,070 B2 | 10/2003 | Leeflang et al. | |
| 6,645,220 B1 | 11/2003 | Huter et al. | |
| 6,645,222 B1 | 11/2003 | Parodi et al. | |
| 6,645,223 B2 | 11/2003 | Boyle et al. | |
| 6,652,555 B1 | 11/2003 | VanTassel et al. | |
| 6,652,556 B1 | 11/2003 | VanTassel et al. | |
| 6,656,351 B2 | 12/2003 | Boyle | |
| 6,673,090 B2 | 1/2004 | Root et al. | |
| 6,676,682 B1 | 1/2004 | Tsugita et al. | |
| 6,689,150 B1 | 2/2004 | VanTassel et al. | |
| 6,692,508 B2 | 2/2004 | Wensel et al. | |
| 6,692,509 B2 | 2/2004 | Wensel et al. | |
| 6,692,513 B2* | 2/2004 | Streeter et al. | 606/200 |
| 6,695,813 B1 | 2/2004 | Boyle et al. | |
| 6,695,858 B1 | 2/2004 | Dubrul et al. | |
| 6,702,834 B1 | 3/2004 | Boylan et al. | |
| 6,706,053 B1 | 3/2004 | Boylan et al. | |
| 6,706,055 B2 | 3/2004 | Douk et al. | |
| 6,730,108 B2 | 5/2004 | Van Tassel et al. | |
| 6,746,469 B2 | 6/2004 | Mouw | |
| 6,818,006 B2 | 11/2004 | Douk et al. | |
| 6,830,579 B2 | 12/2004 | Barbut | |
| 6,837,898 B2 | 1/2005 | Boyle et al. | |
| 6,855,154 B2 | 2/2005 | Abdel-Gawwad | |
| 6,866,677 B2 | 3/2005 | Douk et al. | |
| 6,887,258 B2 | 5/2005 | Denison et al. | |
| 6,896,690 B1* | 5/2005 | Lambrecht et al. | 606/200 |
| 6,902,540 B2 | 6/2005 | Dorros et al. | |
| 6,908,474 B2 | 6/2005 | Hogendijk et al. | |
| 6,911,036 B2 | 6/2005 | Douk et al. | |
| 6,936,060 B2 | 8/2005 | Hogendijk et al. | |
| 6,939,362 B2 | 9/2005 | Boyle et al. | |
| 6,964,670 B1 | 11/2005 | Shah et al. | |
| 6,964,673 B2 | 11/2005 | Tsugita et al. | |
| 6,989,027 B2* | 1/2006 | Allen et al. | 623/2.18 |
| 7,044,958 B2 | 5/2006 | Douk et al. | |
| 7,044,966 B2 | 5/2006 | Svanidze et al. | |
| 7,066,946 B2 | 6/2006 | Douk et al. | |
| 7,101,396 B2 | 9/2006 | Artof et al. | |
| 7,169,164 B2 | 1/2007 | Borillo et al. | |
| 7,172,614 B2 | 2/2007 | Boyle et al. | |
| 7,172,621 B2 | 2/2007 | Theron | |
| 7,214,237 B2 | 5/2007 | Don Michael et al. | |
| 7,217,255 B2 | 5/2007 | Boyle et al. | |
| 7,223,253 B2 | 5/2007 | Hogendijk | |
| 7,232,452 B2 | 6/2007 | Adams et al. | |
| 7,232,453 B2 | 6/2007 | Shimon | |
| 7,241,304 B2 | 7/2007 | Boyle et al. | |
| 7,250,041 B2 | 7/2007 | Chiu et al. | |
| 7,252,675 B2 | 8/2007 | Denison et al. | |
| 7,279,000 B2 | 10/2007 | Cartier et al. | |
| 7,306,575 B2 | 12/2007 | Barbut et al. | |
| 7,322,957 B2 | 1/2008 | Kletschka et al. | |
| 7,326,226 B2 | 2/2008 | Root et al. | |
| 7,331,973 B2 | 2/2008 | Gesswein et al. | |
| 7,338,510 B2 | 3/2008 | Boylan et al. | |
| 7,344,549 B2 | 3/2008 | Boyle et al. | |
| 7,371,249 B2 | 5/2008 | Douk et al. | |
| 7,425,215 B2 | 9/2008 | Boyle et al. | |
| 7,537,600 B2 | 5/2009 | Eskuri | |
| 7,544,202 B2 | 6/2009 | Cartier et al. | |
| 7,572,272 B2 | 8/2009 | Denison et al. | |
| 7,582,100 B2 | 9/2009 | Johnson et al. | |
| 7,585,309 B2 | 9/2009 | Larson | |
| 7,591,832 B2 | 9/2009 | Eversull et al. | |
| 7,604,650 B2 | 10/2009 | Bergheim | |
| 7,842,084 B2 | 11/2010 | Bicer | |
| 2002/0161394 A1 | 10/2002 | Macoviak et al. | |
| 2004/0220609 A1 | 11/2004 | Douk et al. | |
| 2005/0015048 A1 | 1/2005 | Chiu et al. | |
| 2005/0015112 A1 | 1/2005 | Cohn et al. | |
| 2005/0261759 A1 | 11/2005 | Lambrecht et al. | |
| 2006/0173490 A1 | 8/2006 | Lafontaine et al. | |
| 2007/0179590 A1* | 8/2007 | Lu et al. | 623/1.16 |
| 2008/0039786 A1 | 2/2008 | Epstein et al. | |
| 2009/0018498 A1 | 1/2009 | Chiu et al. | |

OTHER PUBLICATIONS

Finite Element Stent Design, M. De Beule, R. Van Impe, P. Verdonck B. Verhegghe, Computer Methods in Biomechanics and Biomedical Engineering, 2005.

US 7,169,126, 01/2007, Zadno-Azizi (withdrawn)

* cited by examiner

PROTECTION DEVICE AND METHOD AGAINST EMBOLIZATION AGENT REFLUX

RELATED APPLICATIONS

The present application claims priority from U.S. Ser. No. 61/266,068 filed Dec. 2, 2009 entitled "Anti-Reflux Protection Device" which is hereby incorporated by reference herein in its entirety.

BACKGROUND OF THE INVENTION

1. Field of Invention

The present invention relates generally to a medical embolizing treatment system. More particularly, the present invention relates to an emboli zing treatment system utilizing a protection device which reduces the reflux of a treatment agent in a blood vessel during an embolization therapy procedure, where the embolization agent is delivered through a catheter to provide therapy to tissue distal via a delivery orifice of the catheter.

2. State of the Art

Embolization, chemo-embolization, and radio-embolization therapy are often clinically used to treat a range of diseases, such as hypervascular liver tumors, uterine fibroids, secondary cancer metastasis in the liver, pre-operative treatment of hypervascular menangiomas in the brain and bronchial artery embolization for hemoptysis. An embolizing agent may be embodied in different forms, such as beads, liquid, foam, or glue placed into an arterial vasculature. The beads may be uncoated or coated. Where the beads are coated, the coating may be a chemotherapy agent, a radiation agent or other therapeutic agent. When it is desirable to embolize a small blood vessel, small bead sizes (e.g., 40 μm-100 μm) are utilized. When a larger vessel is to be embolized a larger bead size (e.g., 100 μm-900 μm) is typically chosen.

While embolizing agent therapies which are considered minimally or limited invasive therapies have often provided good results, they have a small incidence of non-targeted embolization which can lead to adverse events and morbidity. One cause of non-targeted delivery of embolizing agents is reflux in the artery. Reflux occurs where the embolic agent exits the distal end of the catheter and then backflows around the outside of the catheter. This backflow can end up in a healthy organ and damage it.

Reflux can also occur during the administration of the embolization agent, while the artery is still patent. Reflux may also occur when the artery becomes static and injected embolizing agents flow backward.

Additionally, reflux can be a time-sensitive phenomenon. Sometimes, reflux occurs as a response to an injection of the embolic agent, where the reflux occurs rapidly (e.g., in the time-scale of milliseconds) in a manner which is too fast for a human operator to respond. Also, reflux can happen momentarily, followed by a temporary resumption of forward flow in the blood vessel, only to be followed by additional reflux.

FIG. 1 shows a conventional (prior art) embolization treatment in the hepatic artery 106. Catheter 101 delivers embolization agents (beads) 102 in a hepatic artery 106, with a goal of embolizing a target organ 103. It is important that the forward flow (direction arrow 107) of blood is maintained during an infusion of embolization agents 102 because the forward flow is used to carry embolization agents 102 deep into the vascular bed of target organ 103.

Embolization agents 102 are continuously injected until reflux of contrast agent is visualized in the distal area of the hepatic artery. Generally, since embolization agents 102 can rarely be visualized directly, a contrast agent may be added to embolization agents 102. The addition of the contrast agent allows for a visualization of the reflux of the contrast agent (shown by arrow 108), which is indicative of the reflux of embolization agents 102. The reflux may, undesirably, cause embolization agents 102 to be delivered into a collateral artery 105, which is proximal to the tip of catheter 101. The presence of embolization agents 102 in collateral artery 105 leads to non-target embolization in a non-target organ 104, which may be the other lobe of the liver, the stomach, small intestine, pancreas, gall bladder, or other organ.

Non-targeted delivery of the embolic agent may have significant unwanted effects on the human body. For example, in liver treatment, non-targeted delivery of the embolic agent may have undesirable impacts on other organs including the stomach and small intestine. In uterine fibroid treatment, the non-targeted delivery of the embolic agent may embolize one or both ovaries leading to loss of menstrual cycle, subtle ovarian damage that may reduce fertility, early onset of menopause and in some cases substantial damage to the ovaries. Other unintended adverse events include unilateral deep buttock pain, buttock necrosis, and uterine necrosis.

Often, interventional radiologists try to reduce the amount and impact of reflux by slowly releasing the embolizing agent and/or by delivering a reduced dosage. The added time, complexity, increased x-ray dose to the patient and physician (longer monitoring of the patient) and potential for reduced efficacy make the slow delivery of embolization agents sub-optimal. Also, reducing the dosage often leads to the need for multiple follow-up treatments. Even when the physician tries to reduce the amount of reflux, the local flow conditions at the tip of the catheter change too fast to be controlled by the physician, and therefore rapid momentary reflux conditions can happen throughout infusion.

SUMMARY OF THE INVENTION

According to one aspect of the invention, an apparatus is provided that is useful in an embolization procedure and which enables substantially unrestricted forward flow of blood in a vessel and reduces or stops reflux (regurgitation or backward flow) of embolization agents which are introduced into the blood.

In one embodiment, the apparatus which enables substantially unrestricted forward flow in a vessel and which reduces or stops reflux of embolization agents allows the reflux of blood or contrast agent. In another embodiment, the apparatus which enables substantially unrestricted forward flow in a vessel and which reduces or stops reflux of embolization agents and also reduces or stops backward flow of blood.

In a preferred embodiment, the deployable apparatus includes a delivery catheter having a valve coupled to the distal end thereof. The valve includes a plurality of filaments which cross over each other (i.e., are braided) and which have a spring bias to assume a preferred crossing angle relative to each other. In a first state, the valve is preferably kept in a cylindrical arrangement with a diameter substantially equal to the diameter of the delivery catheter. In a second state, the valve is free to open due to the spring bias in the filaments. In the second state, with the proximal end of the valve attached to the delivery catheter, in the bloodstream, if the blood is not flowing distally past the valve, the valve assumes a substantially frustoconical shape. The distal end of the valve is intended to make contact with the walls of the vessel in which it is deployed when blood is not flowing distally past the valve.

According to one aspect of the invention, the valve has a radial force of expansion when in the undeployed state of less than 40 mN.

According to another aspect of the invention, the valve has a time constant of expansion from the cylindrical arrangement to the fully-open position when in a static fluid having a viscosity of approximately 3.2 cP of between 1.0 and 0.01 seconds, and more preferably between 0.50 and 0.05 seconds.

According to a further aspect of the invention, the valve has a Young's modulus of elasticity that is greater than 100 MPa.

According to yet another aspect of the invention, the preferred crossing angle of the valve filaments is approximately 110 degrees.

According to even another aspect of the invention, the filaments of the valve are selected to be of a desired number and diameter such that in an open position, they are capable of trapping embolization agents. By way of example only, the filaments of the valve are selected so that in an open position they present a pore size of 500 µm and are thus capable of preventing reflux of embolizing agent such as beads having a size larger than 500 µm. As another example, the filaments of the valve are selected so that in an open position they present a pore size of 250 µm and are thus capable of preventing reflux of embolizing agent having a size larger than 250 µm.

In one embodiment, the valve filaments are coated with a filter which is formed and attached to the filaments according to any desired manner, such as by spraying, spinning, electrospinning, bonding with an adhesive, thermally fusing, melt bonding, or other method. The filter is preferably arranged to have a desired pore size, although it will be appreciated that the pore size may be non-uniform depending upon the technique in which the filter is formed and attached. By way of example, the pore size of the filter may be approximately 40 µm such that embolizing agents having a characteristic size of more than 40 µm are prevented from refluxing past the valve. By way of another example, the pore size of the filter may be approximately 20 µm such that embolizing agents having a characteristic size of more than 20 µm are prevented from refluxing past the valve. In both cases, blood cells (which have a characteristic size smaller than 20 µm), and contrast agent which has a molecular size smaller than 20 µm will pass through the filter and valve.

According to an additional aspect of the invention, when in a fully-open position where the filaments assume the preferred crossing angle, the valve is adapted to have a distal diameter which is at least twice the diameter of the delivery catheter, and preferably at least five times the diameter of the delivery catheter.

In one embodiment, the filaments are all formed from a polymer. In another embodiment, one or more of the filaments is formed from platinum or platinum-iridium.

In an embodiment where one or more filaments are formed from a polymer, the filaments that are formed from the polymer are melted at their proximal end into the delivery catheter.

According to one aspect of the invention, the valve, which is preferably coupled to the distal end of the delivery catheter, may deployed in any of several manners. Thus, by way of example only, an outer catheter or sleeve extending over the delivery catheter may be used to keep the valve in an undeployed state, and the outer catheter or sleeve may be pulled backward relative to the delivery catheter in order to deploy the valve. Where an outer catheter or sleeve is utilized, the valve may be captured and returned to its undeployed position by moving the delivery catheter proximally relative to the outer catheter or sleeve.

As another example, the distal end of the valve may be provided with loops which are adapted to engage a guidewire which extends through and distal the distal end of the delivery catheter and through the distal loops of the valve. When the guidewire is withdrawn proximally, the valve deploys.

As another example, a knitted sleeve with a control thread can be provided to cover the valve. The control thread, when pulled, causes the knitted sleeve to unravel, thereby releasing the valve.

BRIEF DESCRIPTION OF DRAWINGS

Prior art

DETAILED DESCRIPTION OF THE PREFERRED EMBODIMENTS

Figure 1:
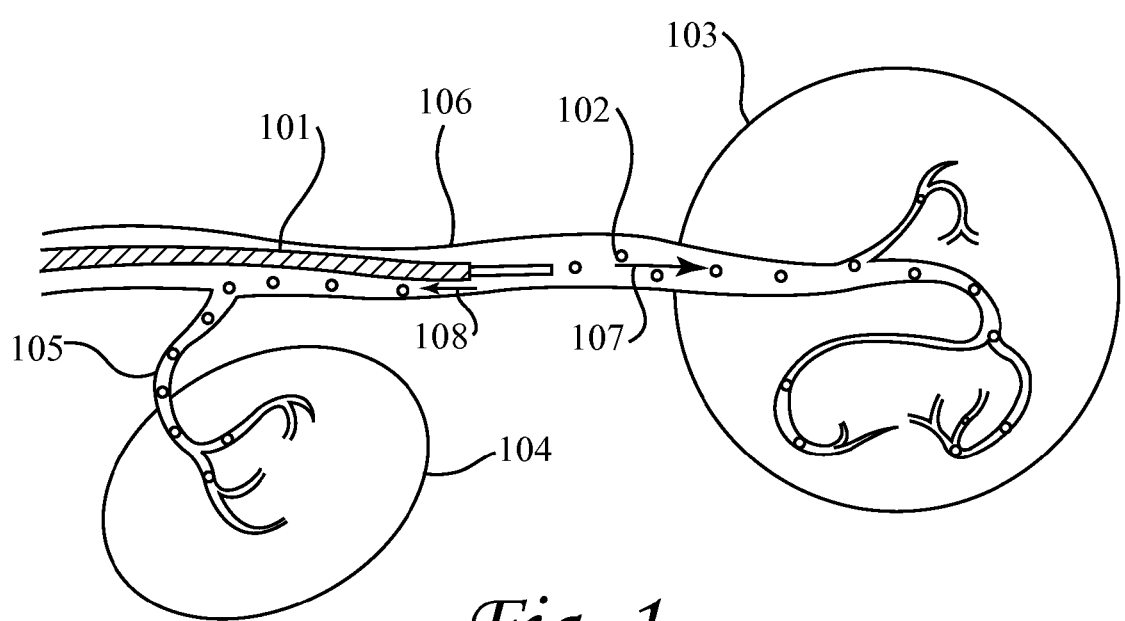
FIG. 1 shows a conventional embolizing catheter in a hepatic artery with embolizing agent refluxing into a non-targeted organ.
Figure 2A:
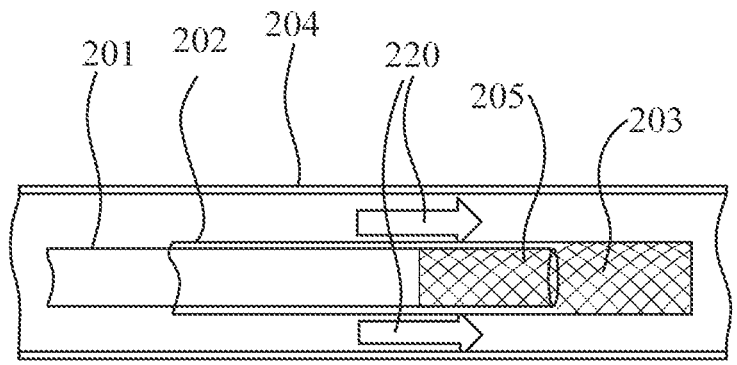
FIGS. 2A-2C are schematic diagrams of a first exemplary embodiment of an apparatus of the invention respectively in an undeployed state, a deployed partially open state with blood passing in the distal direction, and a deployed fully open state where the blood flow is static.
Figure 2B:
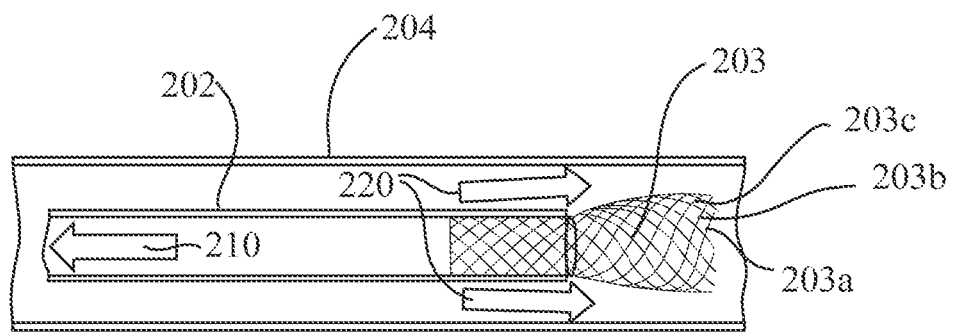
Figure 2C:
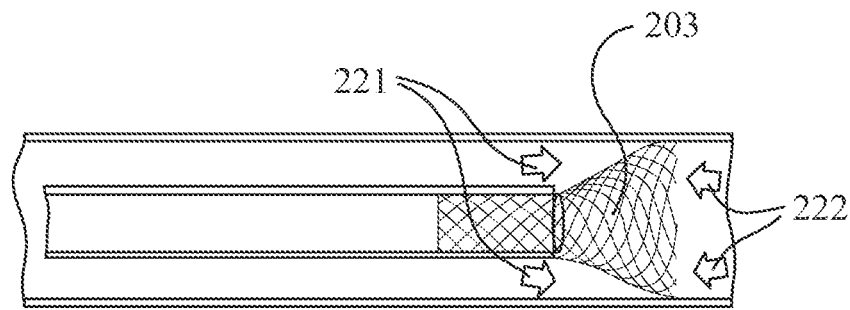

A first exemplary embodiment of the invention is seen in FIGS. 2A-2C. It is noted that FIGS. 2A-2C are not shown to relative size but rather are shown for purposes of explanation. In FIGS. 2A-2C a delivery catheter 201 having a proximal end (not shown) and a distal end 205 is shown positioned within an artery 204. The delivery catheter 201 is adapted for delivery of an embolizing agent from outside the body of the patient (not shown) to a target vessel (artery or vein) in the patient. Attached to the distal end 205 of the catheter 201 is an exemplary embodiment of a valve 203 shown having multiple filaments 203a, 203b, 203c, . . . which are preferably braided and can move relative to each other. As discussed hereinafter, the filaments are spring biased (i.e., they have "shape memory") to assume a desired crossing angle relative to each other so that the valve can assume a substantially frustoconical shape (it being noted that for purposes herein the term "substantially frustoconical" should be understood to include not only a truncated cone, but a truncated hyperboloid, a truncated paraboloid, and any other shape which starts from a circular proximal end and diverges therefrom). Around the catheter 201 is an outer catheter or sleeve 202 which is movable over the delivery catheter 201 and valve 203. If desired, the outer catheter or sleeve 202 can extend the entire length of the delivery catheter. Where the outer catheter or sleeve 202 extends along the entire length of the delivery catheter, it has a proximal end (not shown) which extends proximally and which can be controlled by a practitioner from outside the body of the patient. Alternatively, the outer catheter or sleeve 202 extends only over the distal end of the delivery catheter 201 and valve 203, but is controlled by a control element which extends proximally and which can be controlled by a practitioner from outside the body of the patient.

As seen in FIG. 2A, when the outer catheter or sleeve 202 extends over the valve 203, the multiple filaments are forced into a cylindrical shape. Thus, FIG. 2A shows the braid valve in a retracted or undeployed cylindrical state, with the braid filaments 203a, 203b, 203c . . . attached to a distal end of a catheter 205 and covered by the sleeve 202. Catheter 201 is positioned within an artery 204 that has forward blood flow in the direction of arrows 220. As seen in FIG. 2B, upon retraction of the sleeve 202 in the direction of arrow 210, the non-constrained portion of the valve 203 is freed to expand radially (and retract longitudinally) towards its shape memory position. However, the distally flowing blood (indicated by arrows 220) generates a force that prevents the valve from opening more completely, and prevents the valve from touching the walls of vessel 204. As a result, the valve 203 is maintained in a condition where it is not sufficiently open to block blood flow in the distal or proximal directions. In other words, the forward blood flow causes the braid to lengthen and simultaneously decrease its diameter (relative to a fully open position) to allow fluid to pass between the braid and the vessel wall.

FIG. 2C shows the valve 203 where the bloodstream is in slow forward flow 221, static flow, or reverse flow 222 which might occur after delivery of embolic agents through catheter 201 and past the valve 203. In slow forward flow 221, the force applied by the blood against the filaments of the braided valve is not sufficient to prevent the valve from opening until the valve 203 reaches the wall of the vessel 204. In static flow (no significant movement of blood in either direction), the blood does not apply any forward force. During reverse flow 222, the blood applies a force which helps the valve open. In the fully deployed arrangement of FIG. 2C, the braid valve acts as a filter to stop embolic agents from flowing proximal the valve. However, as discussed in more detail hereinafter, depending upon the pore size of the braid valve 203, blood and contrast agent may be permitted to flow backward through the valve and around the catheter 201 while stopping or significantly reducing the flow of embolic agents.

It should be appreciated by those skilled in the art that the catheter 201 can be any catheter known in the art. Typically, the catheter will be between two and eight feet long, have an outer diameter of between 0.67 mm and 3 mm (corresponding to catheter sizes 2 French to 9 French), and will be made from a liner made of fluorinated polymer such as PTFE or FEP, a braid made of metal such as stainless steel or titanium, or a polymer such as PET or liquid crystal polymer, and a outer coating made of polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream. Sleeve or outer catheter 202 is comprised of a material capable of holding valve braid 203 in a cylindrical configuration and capable of sliding over the valve braid 203 and the catheter 201. Sleeve or outer catheter 202 can be comprised of polyurethane, polyamide, copolymers of polyamide, polyester, copolymers of polyester, fluorinated polymers, such as PTFE, FEP, polyimides, polycarbonate or any other suitable material. The sleeve or outer catheter may also contain a braid composed of metal such as stainless steel or titanium, or a polymer such as PET or liquid crystal polymer, or any other suitable material. The wall thickness of sleeve or outer catheter 202 is preferably in the range of 0.002" to 0.010" with a more preferred thickness of 0.004"-0.006".

The valve 203 is composed of one, two, or more metal (e.g., stainless steel or nitinol) or polymer filaments, which form a substantially frustoconical shape when not subject to outside forces. Where polymeric filaments are utilized, the filaments may be composed of PET, polyethylene-napthalate (PEN), liquid crystal polymer, fluorinated polymers, nylon, polyamide or any other suitable polymer. If desired, when polymeric filaments are utilized, one or more metal filaments may be utilized in conjunction with the polymeric filaments. According to one aspect of the invention, where a metal filament is utilized, it may be of radio-opaque material such that it may be tracked in the body. The valve is capable of expanding in diameter while reducing in length, and reducing in diameter while expanding in length. The valve is preferably composed of shape memory material that is formed and set in a large diameter orientation. As previously mentioned, the valve is preferably held in a small diameter orientation until it is released, and when released by removing the sleeve or other restricting component 202, the distal end of the valve expands to a larger diameter. Where the valve is comprised of multiple filaments, it is preferred that the filaments not to be bonded to each other or at their distal ends so to enable the valve to rapidly open and close in response to dynamic flow conditions.

In the preferred embodiment, the valve is constrained only at its proximal end where it is coupled to the catheter body, while the remainder of the valve can either be constrained (retracted state) by a sleeve or catheter, or partially unconstrained (partially deployed state) or completely unconstrained (completely deployed state). When in the partially or completely unconstrained conditions, depending upon the flow conditions in the vessel, the valve may either reach the walls of the vessel or it may not.

As previously mentioned, the valve diameter should change in response to local flow conditions so as to enable forward flow, but capture embolic agents in brief or prolonged periods of reverse flow. For simplicity, the valve can be considered to exist in two conditions. In a "closed" condition, the valve is not sealed against the vessel wall and blood may flow around the valve in either direction. In an "open" condition, the valve is sealed against the vessel wall and blood must pass through the valve if it is to flow past the valve in either direction.

Three parameters help define the performance and novel nature of the valve: the radial (outward) force of the valve, the time constant over which the valve changes condition from closed to open, and the pore size of the valve.

In a preferred embodiment, the valve expands fully to the vessel wall (i.e., reaches an open condition) when any part of the flow around the braid nears stasis and remains in a closed condition when blood is flowing distally with regular force in the distal direction. More particularly, when the radial force of expansion of the valve is greater than the force from forward blood flow, the valve expands to the vessel wall. However, according to one aspect of the invention, the radial force of expansion of the valve is chosen to be low (as described in more detail below) so that blood flow in the distal direction will prevent the valve from reaching the open condition. This low expansion force is different than the expansion forces of prior art stents, stent grafts, distal protection filters and other vascular devices, which have a sufficiently high radial force to fully expand to the vessel wall in all flow conditions.

The radial force of expansion of a braid is described by Jedwab and Clerc (*Journal of Applied Biomaterials*, Vol. 4, 77-85, 1993) and later updated by DeBeule (De Beule et al. *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0}$$

$$K_2 = \frac{2\cos^2\beta_0}{D_0}$$

$$K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the braid angle ($\beta$), stent diameter ($D_0$), wire thickness (d), and number of filaments (n) impact the radial force of the braided valve.

In one embodiment, with a valve arrangement as shown in FIGS. 2A-2C, the valve 203 is composed of twenty-four polyethylene terephthalate (PET) filaments 203a, 203b, . . . , each having a diameter of 0.004" and pre-formed to an 8 mm diameter mandrel and a braid angle of 110° (i.e., the filaments are spring-biased or have a shape memory to assume an angle of 110° relative to each other). The filaments preferably have a Young's modulus greater than 200 MPa, and the valve preferably has a radial force of less than 40 mN in the fully deployed position (i.e., where the filaments assume their shape memory). More preferably, the valve has a radial force in the fully deployed position of less than 20 mN, and even more preferably the valve has a radial force of approximately 10 mN (where the term "approximately" as used herein is defined to mean±20%) in the deployed position. Where the valve includes a filter as well as the braided filaments (as will be discussed hereinafter with respect to FIGS. 3A and 3B), the braid component preferably has a radial force of less than 20 mN in the fully deployed position, and more preferably a radial force of less than 10 mN, and even more preferably a radial force of approximately 5 mN. This compares to prior art embolic capture devices such as the ANGIOGUARD (a trademark of Cordis Corporation), and prior art Nitinol stents and stent-grafts which typically have radial forces of between 40 mN and 100 mN in their fully deployed positions.

According to one aspect of the invention, the valve opens and closes sufficiently quickly to achieve high capture efficiency of embolic agents in the presence of rapidly changing flow direction. In one embodiment, the valve moves from a fully closed (undeployed) position to a fully open position in a static fluid (e.g., glycerin) having a viscosity approximately equal to the viscosity of blood (i.e., approximately 3.2 cP) in 1/15 second. For purposes herein, the time it takes to move from the fully closed position to the fully open position in a static fluid is called the "time constant". According to another aspect of the invention, the valve is arranged such that the time constant of the valve in a fluid having the viscosity of blood is between 0.01 seconds and 1.00 seconds. More preferably, the valve is arranged such that the time constant of the valve in a fluid having the viscosity of blood is between 0.05 and 0.50 seconds. The time constant of the valve may be adjusted by changing one or more of the parameters described above (e.g., the number of filaments, the modulus of elasticity of the filaments, the diameter of the filaments, etc.).

As will be appreciated by those skilled in the art, the braid geometry and material properties are intimately related to the radial force and time constant of the valve. Since, according to one aspect of the invention, the valve is useful in a variety of arteries of different diameters and flow conditions, each implementation can have a unique optimization. By way of example only, in one embodiment, the valve has ten filaments, whereas in another embodiment, the valve has forty filaments. Preferably, the filament diameter is chosen in the range of 0.001" to 0.005", although other diameters may be utilized. Preferably, the pitch angle (i.e., the crossing angle assumed by the filaments in the fully open position—the shape memory position) is chosen in the range of 90° to 145°, although other pitch angles may be used. Preferably, the Young's modulus of the filament is at least 100 MPa, and more preferably at least 200 MPa.

According to another aspect of the invention, the valve is chosen to have a pore size which is small enough to capture (filter) embolic agents in the blood stream as the blood passes through the valve. Where large embolic agents (e.g., 500 µm) are utilized, it may be possible for the filaments of the valve to act directly as a filter to prevent embolic agents from passing through the valve (provided the filaments present pores of less than, e.g., 500 µm). Alternatively, a filter may be added to the filament structure. Such a separate filter is particularly useful where smaller embolic agents are utilized.

Figure 3A:
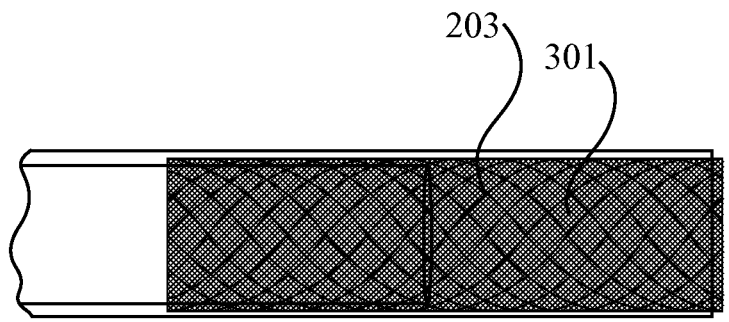
FIGS. 3A and 3B are schematic diagrams of an exemplary embodiment of a valve having a braid component that is covered by a filter component in respectively an undeployed state and a deployed state.
Figure 3B:
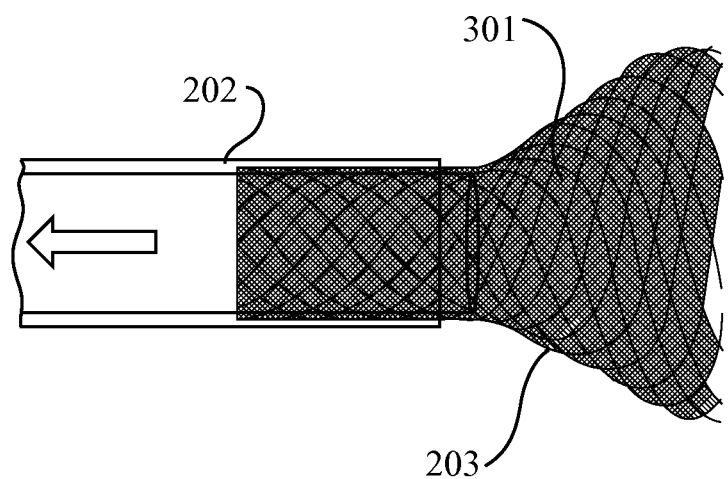

FIG. 3A shows a braid valve 203 at the distal end of a catheter 201 and having a filter 301 that is added to the braid structure 203. The filter can be placed onto the braid by spraying, spinning, electrospinning, bonding with an adhesive, thermally fusing, mechanically capturing the braid, melt bonding, or any other desired method. The filter can either be a material with pores such as ePTFE, a solid material that has pores added such as polyurethane with laser drilled holes, or the filter can be a web of very thin filaments that are laid onto the braid. Where the filter 301 is a web of thin filaments, the characteristic pore size of the filter can be tested determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In the preferred embodiment a material capable of being electrostatically deposited or spun is used to form a filter on the braid, with the preferred material being capable of bonding to itself. The filter may be made of polyurethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process. FIG. 3B shows the valve in the deployed state, with outer catheter 202 retracted proximally (as indicated by the arrow) where the braid 203 and the filter 301 are expanded.

According to one aspect of the invention, the filter 301 has a characteristic pore size between 10 µm and 500 µm. More preferably, the filter 301 has a characteristic pore size between 15 µm and 100 µm. Even more preferably, the filter 301 has a characteristic pore size of less than 40 µm and more preferably between 20 µm and 40 µm. Most desirably, the filter 301 is provided with a characteristic pore size that will permit blood and contrast agent to pass therethrough while blocking passage of embolizing agent therethrough. By allowing regurgitating blood and contrast agent to pass through the filter in a direction from distal the valve toward the proximal end of the valve, the contrast agent may be used to indicate when the target site is fully embolized and can serve to identify a clinical endpoint of the embolization procedure. Therefore, according to one aspect of the invention, the valve allows the reflux of the contrast agent as an indicator of the clinical endpoint while preventing the reflux of the embolization agents at the same time.

According to one aspect of the method of the invention, the valve is capable of endovascular deployment. The valve is preferably coupled to the distal end of a catheter. When the distal end of the catheter is in the correct location for treatment, the valve is deployed. Preferably, with the valve deployed, embolization agents are delivered distally through the catheter into the vessel. Delivery of the embolization agents will tend to result in the slowing or stoppage of blood flow in the distal direction and a resultant expansion of the valve from an initial diameter which is smaller or equal to the outer diameter of the catheter (i.e., its undeployed position) to a final diameter (its open position) which is preferably at least twice, and more typically four to ten times the outer diameter of the catheter. In its open position, the valve stops embolization agents from traveling past the valve (between the catheter wall and the vessel wall) in a proximal direction. According to one aspect of the invention, the valve is preferably capable of being refracted into its closed position after the embolization treatment procedure is completed.

It is important to note that the valve is a dynamic element that opens and closes based on local flow conditions. In normal flow conditions, the flow pressure is sufficient to overcome the weak biasing force, thereby forcing the valve into a closed position such that it does not contact the vascular wall. In static or reverse flow, the biasing force of the valve filaments causes the valve to an open position where it preferably is in full contact with the vascular wall, thereby restricting reflux of embolizing agents, while preferably permitting reflux of blood and contrast agents.

According to one aspect of the invention, deployment of the valve is controlled from the proximal end of the catheter. In some embodiments, a control wire or a set of two or more control wires extending from the proximal end of the catheter to the distal end of the catheter may be used and controlled by the practitioner to deploy and optionally retract the valve. In some embodiments, a control thread extending from the proximal end of the catheter to the distal end of the catheter is used to unravel fabric covering the valve in order to deploy the valve. In some embodiments, an outer catheter that extends the length of the catheter to which the valve is coupled, covers the valve and during deployment is pulled backward to allow the valve to expand. In some embodiments, an outer sleeve that is coupled to a control element that extends the length of the catheter, covers the valve and during deployment is pulled backward by the control element to allow the valve to expand. In some embodiments, the valve is coupled to a guidewire, and removal of the catheter guidewire initiates deployment of the valve. The control wires, threads, sleeves, etc. may be of standard length, ranging, for example, from 2 to 8 feet long.

Figure 4A:
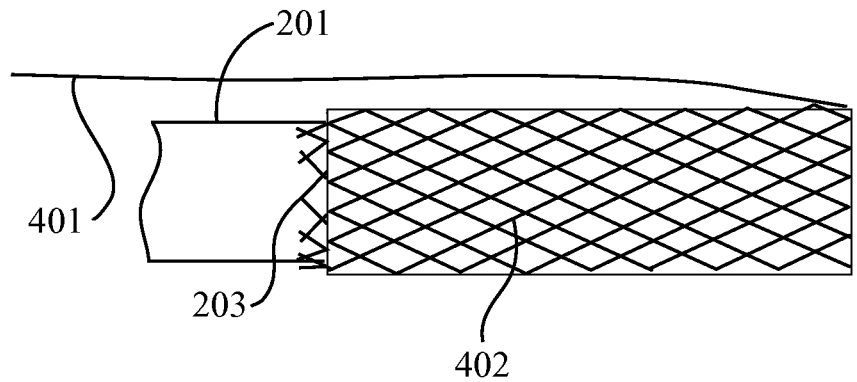
FIGS. 4A-4C are schematic diagrams of the exemplary embodiment of a valve of FIGS. 3A and 3B covered by a weft knit respectively in an undeployed state, a partially deployed state, and a more fully deployed state.
Figure 4B:
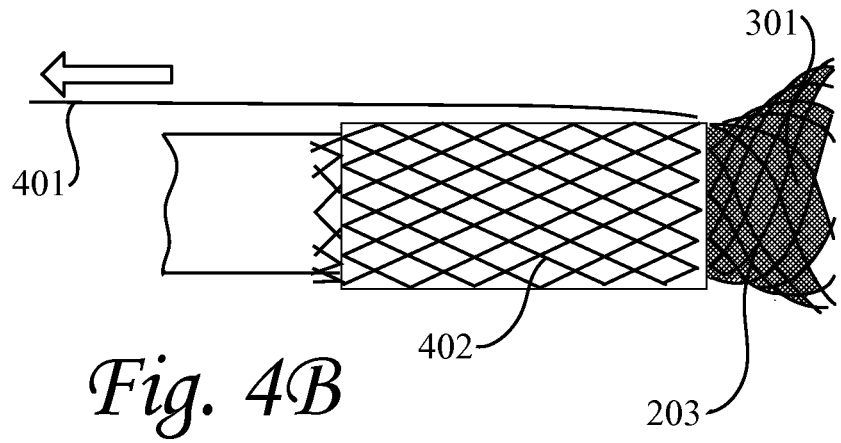
Figure 4C:
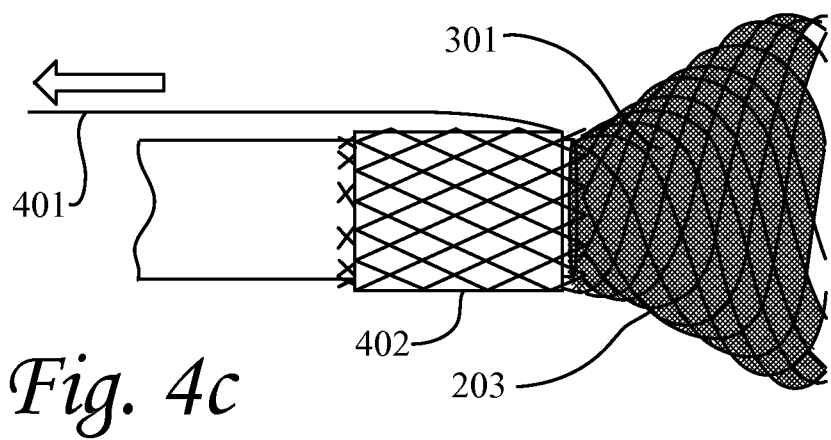

As previously mentioned, the deployment of the valve can be achieved in a variety of manners. As was described in FIG. 2, the valve can be deployed by moving an outer catheter or sleeve that covers the valve. In that embodiment, the valve can be recaptured by the outer catheter or sleeve by moving the catheter or sleeve distally or the delivery catheter and valve proximally. In another embodiment, and as seen in FIGS. 4A-4C, the valve is released by irreversibly removing (unraveling) a knitted sleeve (weft knit) 402 that covers the valve 203 (shown with filter 301). More particularly, as seen in FIG. 4A, the valve 203 is attached to the distal end of the catheter 201. On top of the valve is a weft knit sleeve 402. A control thread 401 is attached to the weft knit and extends to the proximal end of the catheter. In one embodiment the unravelable knit is composed of polyester of a thickness between 10 µm and 60 µm. The knit can be a textile sheath that is held under tension. FIG. 4B shows the deployment of the valve by pulling on the control thread 401. In one embodiment the thread 401 is connected to the distal end of the knit sleeve 402 and releases the valve by first removing material from the distal end of the sleeve 402. As the control thread 401 is pulled back and the sleeve is reduced in size, the distal end of the valve 203 having filter 301 is free to open. The weft knit sleeve 402 may be partially or fully removed to allow the physician control of the diameter or length of the valve. In FIG. 4C the weft knit is more fully removed enabling more of the length of the valve 203 and filter 301 to be free. In another embodiment the thread is attached to the middle or proximal end of the sleeve, and releases the valve by first removing material from the proximal end or from the middle of the sleeve.

Figure 5A:
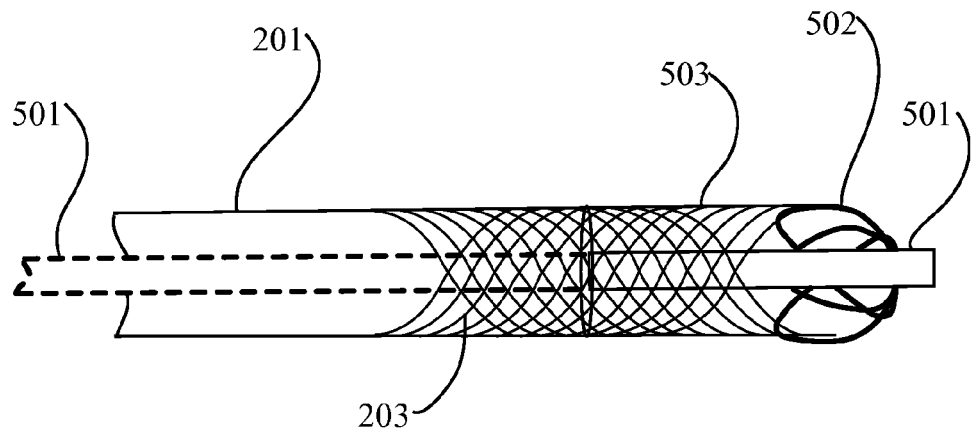
FIGS. 5A-5B are schematic diagrams showing an exemplary embodiment of a valve that can be deployed by movement of a guidewire.
Figure 5B:
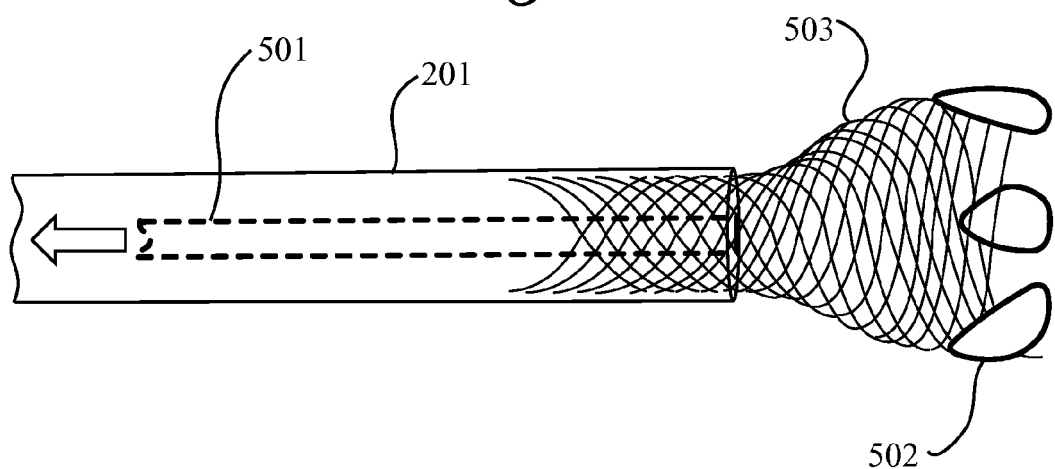

Turning now to FIGS. 5A and 5B, in another embodiment, a guidewire 501 can be used to deploy the valve 503. More particularly, valve 503 is provided with loops 502, which are attached at or near the distal end of the filaments of the valve 503. The loops 502 may be integral with the filaments or may be made of a separate material and attached to the filaments. As seen in FIG. 5A, the loops 502 are looped over the distal end of the guidewire 501 which extends through the lumen of the catheter 201. The loops at the end of the valve 502 are looped around the guidewire 501 while the catheter 201 and guidewire 501 are advanced through the vasculature. In this manner, the distal end of the valve is maintained in a closed position. When the guidewire 501 is withdrawn proximally as denoted by the arrow in FIG. 5B, the distal loops 502 are released, and the valve 503 is deployed.

Figure 6A:
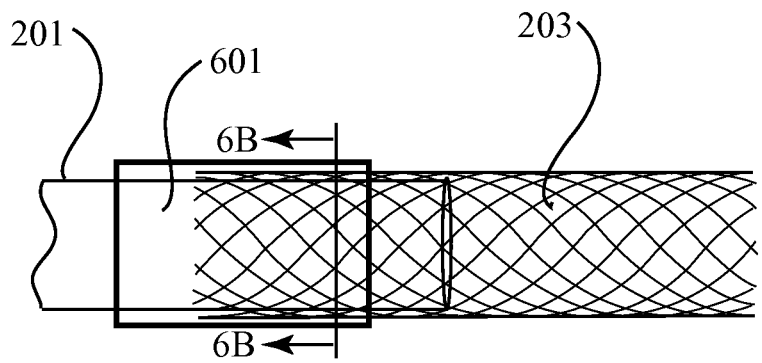
FIGS. 6A-6D show two exemplary methods of attaching the mesh component of the valve to a catheter.
Figure 6B:
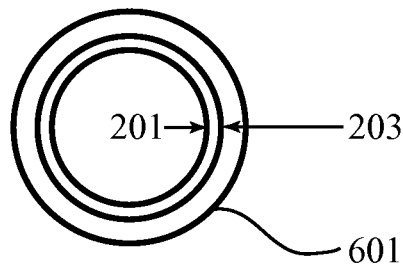

According to one aspect of the invention, the valve of any embodiment of the invention is attached to the distal end of the catheter in any of several manners. As seen in FIG. 6A, the valve 203 is attached to the catheter 201 by a sleeve 601 which overlies the proximal end of the valve 203 and extends proximal the proximal end of the valve 203 over the catheter 201. FIG. 6B shows a cross-sectional view of the catheter 201, valve 203, and sleeve 601. The sleeve 601 is bonded or mechanically held by a heat shrink process or other mechanical process to the catheter 201, and thus holds the distal end of the valve 203 on the catheter 201 by trapping the distal end of the valve between the catheter 201 and the sleeve 601.

Figure 6C:
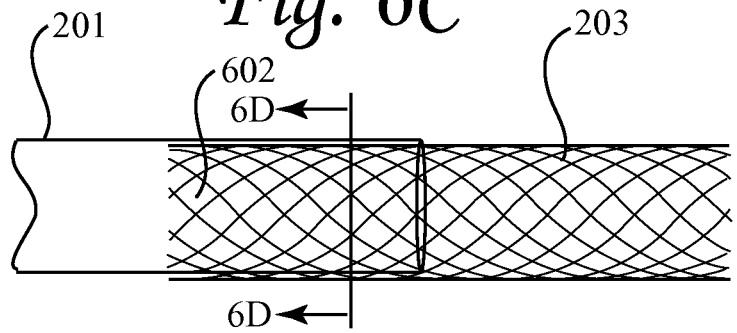
Figure 6D:
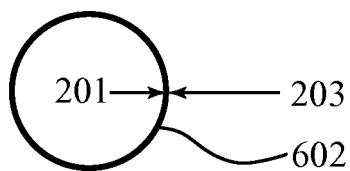

In one preferred embodiment, the valve is fused into the catheter. More particularly, as seen in FIG. 6C the valve 203 fused into the catheter 201 such that at the region 602 where the valve and catheter are fused, there is at most a minimal change to the inner or outer diameter of the catheter 201. FIG. 6D shows a cross-sectional view of the fused valve, where the catheter 201, valve 203 and fused region 602 are all of the same diameter. Fusion of the catheter and valve can be achieved by thermally melting the valve, melting the catheter, melting both the valve and the catheter, or by a chemical process.

Figure 7A:
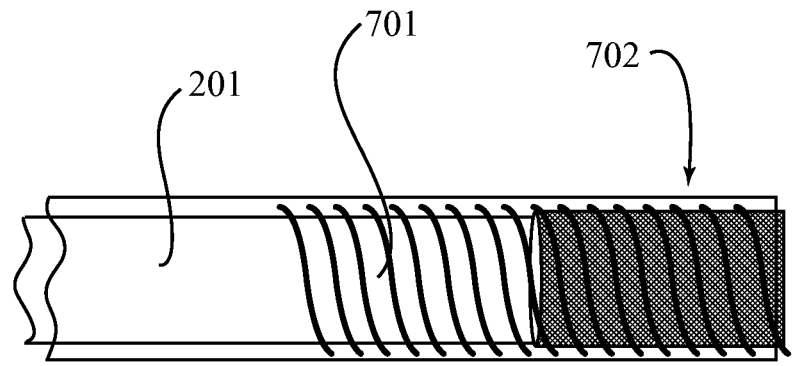
FIGS. 7A-7B show an exemplary embodiment of a valve composed of a single shape memory filament and a filter.
Figure 7B:
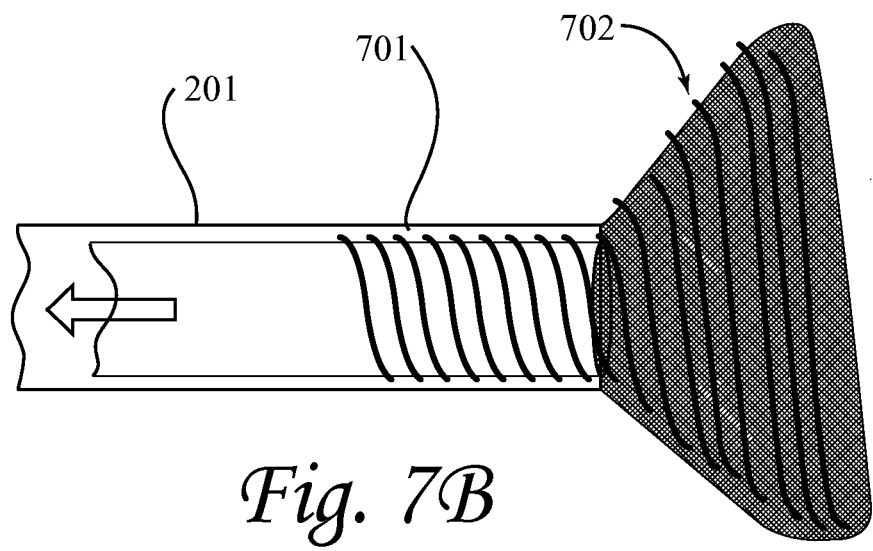

Turning now to FIGS. 7A and 7B, a valve 702 composed of a single filament coil is seen. The coil may be made of metal or polymer, and preferably the filament is a shape memory polymer. FIG. 7A shows a coil valve 701 in the retracted state on a catheter 201. The coil valve is provided with a filter 702 on its distal end. FIG. 7B shows the coil valve in the deployed state, where the valve 701 and the filter 702 are expanded at the distal end. Any of a variety of methods as previously disclosed can be used in deploying the valve.

In any of the embodiments described herein the valve may include textured portions that extend into or engage with the artery wall to reduce or inhibit proximal or distal movement of the valve relative to the vessel wall.

In any of the embodiments described herein the components of the valve may be coated to reduce friction in deployment and retraction. The components may also be coated to reduce thrombus formation along the valve or to be compatible with therapeutics, biologics, or embolics. The components may be coated to increase binding of embolization agents so that they are removed from the vessel during retraction.

According to one aspect of the invention, the catheter body and mesh may be separately labeled for easy visualization under fluoroscopy. The catheter body can be labeled by use of any means shown in the art; for example, compounding a radio-opaque material into the catheter tubing. The radio-opaque material can be barium sulfate, bismuth subcarbonate or other material. Alternatively or additionally, radio-opaque rings can be placed or crimped onto the catheter, where the rings are made of platinum, platinum iridium, gold, tantalum, and the like. The valve may be labeled by crimping a small radio-opaque ring on one or a plurality of filaments. Alternatively or additionally, radio-opaque medium can be compounded into the materials of the braid and the filter. Or, as previously described, one or more of the filaments may be chosen to be made of a radio-opaque material such as platinum iridium.

In the preferred embodiment, the valve is attached to a catheter which may be a single lumen or a multi-lumen catheter. Preferably, the catheter has at least one lumen used to deliver the embolization agents. According to other embodiments, however, the catheter may provided with a lumen which either serves to store the valve before deployment or through which the valve can be delivered. Where control wires are utilized to control the valve, an additional lumen may be provided, if desired, to contain the control wires for deployment and retraction. An additional lumen may also be used to administer fluids, e.g., for flushing the artery after the administration of embolization agents, or for controlling a balloon which could be used in conjunction with the valve.

There have been described and illustrated herein multiple embodiments of devices and methods for reducing or preventing reflux of embolization agents in a vessel. While particular embodiments of the invention have been described, it is not intended that the invention be limited thereto, as it is intended that the invention be as broad in scope as the art will allow and that the specification be read likewise. Thus while particular deployment means for the protection valve have been described, such as a catheter, a sleeve and control element, a fabric sleeve with a control thread, etc., it will be appreciated that other deployment mechanisms such as balloons, absorbable sleeves, or combinations of elements could be utilized. Likewise, while various materials have been listed for the valve filaments, the valve filter, the catheter, and the deployment means, it will be appreciated that other materials can be utilized for each of them. Also, while the invention has been described with respect to particular arteries of humans, it will be appreciated that the invention can have application to any blood vessel of humans and animals. Further, the embodiments have been described with respect to their distal ends because their proximal ends can take any of various forms, including forms well known in the art. By way of example only, the proximal end can include two handles with one handle connected to the inner (delivery) catheter, and another handle connected to an outer catheter or sleeve or actuation wire or string. Movement of one handle in a first direction relative to the other handle can be used to deploy the valve, and where applicable, movement of that handle in an opposite second direction can be used to recapture the valve. Depending upon the handle arrangement, valve deployment can occur when the handles are moved away from each other or towards each other. As is well known, the handles can be arranged to provide for linear movement relative to each other or rotational movement. If desired, the proximal end of the inner catheter can be provided with hash-marks or other indications at intervals along the catheter so that movement of the handles relative to each other can be visually calibrated and give an indication of the extent to which the valve is opened. It will therefore be appreciated by those skilled in the art that yet other modifications could be made to the provided invention without deviating from its spirit and scope as claimed.

We Claim:

1. An endovascular filter-valve device for reducing a reflux of an embolizing agent in a vessel during an embolization therapy procedure, the vessel having a vessel wall, the device comprising:

an elongated delivery catheter having a proximal end and a distal end defining an open tip, said delivery catheter capable of delivering the embolizing agent through said open tip of said distal end;

a substantially frustoconical valve having a proximal end and a distal end, said valve fixed at its proximal end to said distal end of said catheter such that embolizing agent delivered through said delivery catheter feeds into said proximal end of said valve, said valve having a plurality of filaments in the form of a braid, said valve configured and biased to radially expand from an undeployed state to a deployed state, said valve opening from said undeployed state to a completely open state in less than one second in an at-rest fluid having a viscosity of 3.2 cP; and a filter formed of a material separate from said braid and fully integrated with said valve from said proximal end to said distal end of said valve, said filter having pores of a characteristic diameter of less than 500 μm, wherein once said valve is in said deployed state in the vessel, said valve is dynamically movable between an expanded valve-open configuration and a collapsed valve-closed configuration depending on the local biological fluid pressure about said valve, and when the fluid pressure is higher on a proximal side of said valve, said valve is in said valve-closed configuration in which said distal end of said valve assumes a first diameter smaller than the diameter of the vessel such that fluid flow about said valve and said filter is permitted, and when said pressure is higher on a distal side of said valve, said valve is in said valve-open configuration in which said distal end of said valve assumes a second diameter relatively larger than said first diameter, and in which said valve contacts the vessel wall and said characteristic diameter of said pores of said filter renders said filter impermeable to the embolic agent such that the valve is thereby adapted to reduce reflux, wherein integration of said filter and said valve causes both of said filter and said valve to change shape and move together between said valve-open and valve-closed configurations as fluid pressure conditions about said valve change.

2. A device according to claim 1, wherein:
said plurality of filaments includes a plurality of crossing filaments defining a braid angle of less than 70 degrees when in said undeployed state.

3. A device according to claim 2, wherein:
said braid angle is approximately 110 degrees when said valve is in a fully open position.

4. A device according to claim 1, wherein:
said valve in a fully open position has a diameter at least twice said outer diameter of said catheter.

5. A device according to claim 1, wherein:
said filaments have a filament diameter of between 0.001" to 0.005".

6. A device according to claim 1, further comprising:
a deployment element controllable from said proximal end of said catheter, said deployment element adapted to hold said valve in said undeployed state and to release said valve from said undeployed state.

7. A device according to claim 6, wherein:
said deployment element is an outer catheter extending around said delivery catheter and said valve.

8. A device according to claim 1, wherein:
said plurality of filaments include a plurality of polymeric filaments which form a substantially frustoconical shape when said valve is in said deployed state.

9. A device according to claim 8, wherein:
said valve further comprises at least one metal filament.

10. A device according to claim 1, wherein:
said plurality of filaments comprises a plurality of crossing filaments which are not bonded to each other where they cross.

11. A device according to claim 1, wherein:
said plurality of filaments comprises between ten and forty filaments.

12. A device according to claim 1, wherein:
said plurality of filaments is comprised of a material chosen from polyethylene terephthalate (PET), polyethylene-napthalate (PEN), liquid crystal polymer, stainless steel, nitinol, fluorinated polymers, nylon, polyamide, platinum or platinum-iridium.

13. A device according to claim 1, wherein:
said filter is chosen from (i) a material having pores, (ii) a solid material having pores formed therein, and (iii) a web of material coupled to said at least one filament by spraying, spinning, electro-spinning, bonding with an adhesive, thermally fusing, mechanically capturing the braid or melt bonding.

14. A device according to claim 1, wherein:
said filter has pores having a characteristic size of approximately 40 μm or less.

15. A device according to claim 1, wherein:
said filter is comprised of a material soluble in a solvent.

16. A device according to claim 15, wherein:
said filter is comprised of a material selected from a group consisting of polyurethane, polyolefin, polyester, fluoropolymers, acrylic polymers, acrylates, and polycarbonates.

17. A device according to claim 1, wherein:
each of said plurality of filaments has a Young's modulus of elasticity greater than 200 MPa.

18. A device according to claim 1, wherein:
said valve opens from said undeployed state to a completely open state in between 0.05 and 0.50 seconds in an at-rest fluid having a viscosity of 3.2 cP.

19. A device according to claim 1, wherein:
said valve having a radial force of expansion when in said fully open state of less than 20 mN.

20. A device according to claim 1, wherein:
said proximal end of said valve is fused relative to said catheter.

21. A device according to claim 1, wherein:
each of plurality of filaments has a Young's modulus of elasticity greater than 100 MPa.

22. An endovascular filter-valve device for reducing a reflux of an embolizing agent in a vessel during an embolization therapy procedure, the vessel having a vessel wall, the device comprising:
an elongated delivery catheter having a proximal end and a distal end defining an open tip and capable of delivering the embolizing agent through said open tip of said distal end;
a substantially frustoconical valve having a proximal end and a distal end, said valve fixed at its proximal end to said distal end of said catheter such that embolizing agent delivered through said delivery catheter feeds into said proximal end of said valve, said valve having a plurality of filaments and a filter formed of a material separate from said plurality of filaments and coupled to said plurality of filaments from said proximal end to said distal end of said valve, said valve configured and biased to radially expand from an undeployed state to a deployed state,
said valve opening from said undeployed state to a completely open state in between 0.05 and 0.50 seconds in an at-rest fluid having a viscosity of 3.2 cP; and
said filter fully integrated with said valve, said filter having pores of a characteristic diameter of less than approximately 40 μm thereby reducing reflux of the embolizing agent in the vessel by inhibiting the embolizing agent from moving through said pores when said valve is in said deployed state,
wherein once said valve is in said deployed state in the vessel, said valve is dynamically movable between an expanded valve-open configuration and a collapsed valve-closed configuration depending on the local biological fluid pressure about said valve, and
when the fluid pressure is higher on a proximal side of said valve, said valve is in said valve-closed configuration in which said distal end of said valve assumes a first diameter that permits fluid flow about said valve and said filter, and
when said pressure is higher on a distal side of said valve, said valve is in said valve-open configuration in which said distal end of said valve assumes a second diameter relatively larger than said first diameter, and in which said valve contacts the vessel wall and said characteristic diameter of said pores of said filter renders said filter impermeable to the embolic agent such that the valve is thereby adapted to reduce reflux,
wherein integration of said filter and said valve causes both of said filter and said valve to change shape and move together between said valve-open and valve-closed configurations as fluid pressure conditions about said valve change.

23. A device according to claim 22, wherein:
said plurality of filaments cross each other to define a braid angle, and in said undeployed state, said braid angle is less than 70 degrees, and in said fully open position, said braid angle is approximately 110 degrees.

24. A device according to claim 23, wherein:
said valve in said fully open position has a diameter at least twice said outer diameter of said catheter, and
said at least one filament has a filament diameter of between 0.001" to 0.005".

25. A device according to claim 22, further comprising:
a deployment element controllable from said proximal end of said catheter, said deployment element adapted to hold said valve in said undeployed state and to release said valve from said undeployed state.

26. A device according to claim 22, wherein:
said proximal end of said valve is fused relative to said catheter.

27. An endovascular device for reducing a reflux of an embolizing agent in a vessel during an embolization therapy procedure, the vessel having a vessel wall, the device comprising:
an elongated delivery catheter having a proximal end and a distal end defining an open tip and capable of delivering the embolizing agent through said open tip of said distal end;
a substantially frustoconical integrated filter-valve having a proximal end and a distal end, said proximal end of said filter-valve permanently collapsed into contact with said distal end of said catheter such that embolizing agent delivered through said delivery catheter feeds into said proximal end of said filter-valve, said filter-valve having a plurality of braided first filaments configured and biased to radially expand from an undeployed state to a deployed state, a web of second filaments electrospun onto said braided first filaments to define pores of a characteristic diameter of less than approximately 40 μm thereby reducing reflux of the embolizing agent in the vessel by inhibiting the embolizing agent from moving through said pores when said filter-valve is in said deployed state,
wherein because said second filaments are electrospun onto said first filaments, said web of said filaments at all times assumes a same shape as said braided first filaments,
said filter-valve opening from said undeployed state to a completely open state in between 0.05 and 0.50 seconds in an at-rest fluid having a viscosity of 3.2 cP; and
wherein once said filter-valve is in said deployed state in the vessel, said filter-valve is dynamically movable between an expanded valve-open configuration and a collapsed valve-closed configuration depending on the local biological fluid pressure about said filter-valve, and
when the fluid pressure is higher on a proximal side of said filter-valve, said filter-valve is in said valve-closed configuration in which said distal end of said filter-valve assumes a first diameter smaller than a diameter of the vessel to thereby permit fluid flow about the filter-valve, and
when said pressure is higher on a distal side of said filter-valve, said filter-valve is in said valve-open configuration in which said distal end of said filter-valve assumes a second larger diameter sized to contact the vessel wall and said characteristic diameter of said pores of said filter-valve renders said filter-valve impermeable to the embolic agent such that the filter-valve is thereby adapted to reduce reflux,
wherein filter-valve move as a unit between said valve-open and valve-closed configurations as fluid pressure conditions about said filter-valve change.

* * * * *